US 6,579,985 B1

(12) United States Patent
Hill

(10) Patent No.: US 6,579,985 B1
(45) Date of Patent: Jun. 17, 2003

(54) PREPARATION OF CODEINE FROM MORPHINE

(75) Inventor: Lloyd P. Hill, St. Louis, MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 10/274,702

(22) Filed: Oct. 21, 2002

(51) Int. Cl.$^7$ ............................................. C07D 489/02
(52) U.S. Cl. ......................................................... 546/44
(58) Field of Search ........................................... 546/44

(56) References Cited

U.S. PATENT DOCUMENTS 4,764,615 A * 8/1988 Ayyangar et al. .............. 546/44
6,204,337 B1 * 3/2001 Corcoran et al. ......... 525/332.2

* cited by examiner

Primary Examiner—Patricia L. Morris

(57) ABSTRACT

An improved process for the preparation of codeine from morphine comprises the steps of a) reacting morphine with a methylating agent in the presence of a hydrocarbon solvent at a temperature of 100 to 215° C. under reflux conditions such that approximately 50% or more of the hydrocarbon solvent is returned to the reaction mixture to substantially avoid the formation of codeine methyl ether; and b) recovering codeine from the reaction mixture. The process may include step a) above followed by b) cooling the reaction mixture to approximately 85° C. and adding water to terminate the reaction; c) raising the pH of the reaction mixture to approximately 11; d) separating the hydrocarbon solvent phase containing codeine and dimethylaniline; and e) adding a dilute mineral or organic acid and approximately 6 to 7 times the volume of water for each volume of hydrocarbon solvent to separate dimethylaniline and codeine.

20 Claims, No Drawings

PREPARATION OF CODEINE FROM MORPHINE

BACKGROUND OF THE INVENTION

This invention relates to the preparation of codeine from morphine and, more particularly, to an improved process for the preparation of codeine which provides for more complete control over the formation of the methylated by-product codeine methyl ether and for a more thorough separation of dimethylaniline and codeine.

Codeine is widely used as an analgesic and is the methyl ether of morphine. While it occurs naturally in opium to a small extent, it has been prepared synthetically by methylation of the phenolic hydroxyl group in morphine. Thus, it is known to prepare codeine by the reaction of morphine with a methylating agent such as dimethyl sulfate or trimethylphenyl ammonium ethoxide or trimethylphenyl ammonium hydroxide in the presence of a base such as aqueous sodium hydroxide, or alcoholic sodium ethoxide. See W. R. Heumann, Bulletin on Narcotics, Vol. 10, No. 3, pp. 15–17 (1958); U.S. Pat. No. 4,764,615 and U.S. Pat. No. 6,204,337. Modified conditions of the process described by Heumann have been used commercially for some years.

Currently employed processes suffer from significant yield loss, great recycle volume, high operator exposure, and extensive cycle times. The yield loss occurs partly from the current need to remove unreacted morphine and color bodies through precipitation, salt crystalilizations, and carbon treatment. Most of the precipitation and crystallization steps require manual digging of a centrifuge or filter. This creates much operator exposure and greater reliance on personal protection equipment. Allergic symptoms from the narcotics can result through extended exposure. Repetitive motion injuries can also occur from the manual digging.

There remains a need for further improvements in the preparation of codeine from morphine in order to more fully control the formation of the undesired by-product codeine methyl ether, and more efficiently provide for the removal of unreacted morphine and for the separation of dimethylaniline from codeine.

SUMMARY OF THE INVENTION

Among the several objects of the invention may be mentioned the provision of an improved process for preparing codeine from morphine; the provision of such a process in which formation of the by-product codeine methyl ether is more fully controlled; the provision of such an improved process in which removal of unreacted morphine is more efficiently achieved; and the provision of such an improved process which results in the more efficient production of codeine from morphine and overcomes the significant yield loss, great recycle volume and extensive cycle times of prior art processes. Other objects and features will be in part apparent and in part pointed out hereinafter.

Briefly, the present invention is directed to a process for the preparation of codeine from morphine which comprises the steps of a) reacting morphine with a methylating agent in the presence of a hydrocarbon solvent at a temperature of approximately 100 to 115° C. under reflux conditions such that approximately 50% or more of the hydrocarbon solvent is returned to the reaction mixture to substantially avoid the formation of codeine methyl ether; and b) recovering codeine from the reaction mixture. The present invention is also directed to such a process in which step a) above is followed by b) cooling the reaction mixture to approximately 85° C. and adding water to terminate the reaction; c) raising the pH of the reaction mixture to approximately 11; d) separating the hydrocarbon solvent phase containing codeine and dimethylaniline from the aqueous phase containing unreacted morphine; and e) adding a dilute mineral or organic acid and approximately 6 to 7 times the volume of water for each volume of hydrocarbon solvent to effect a separation of dimethylaniline and codeine.

DETAILED DESCRIPTION OF THE PREFERRED EMBODIMENTS

In accordance with the present invention, it has now been found that a more efficient process for the production and purification of codeine from morphine may be achieved through certain improved process conditions. In the first step of known processes such as that described in Heumann's publication for preparing codeine from morphine, a methylating agent such as trimethylphenyl ammonium ethoxide in ethanol is added to a morphine-toluene or other hydrocarbon solvent slurry. At reaction temperatures of 90° C. and above, the ethanol and toluene are stripped off. Toluene and ethanol form a binary azeotrope of 32 wt % ethanol which boils at 76.7° C. During co-distillation of ethanol and toluene, it has been found in accordance with this invention that with sufficient reflux return, ethanol (b.pt.=78.5° C.) and toluene (b.pt.=110.6° C.) can be separated returning the bulk of the toluene to the reaction mixture. More particularly, it has been found that when reflux conditions are such that at least 50% or more of the toluene is returned to the reaction mixture, the over concentration of codeine in toluene is avoided thereby preventing the formation of the methylated by-product of codeine, codeine methyl ether. In general, the provision of two theoretical plates in the overhead condenser will insure adequate toluene in the reaction mixture and control the formation of codeine methyl ether.

The methylation reaction is carried out at a temperature of approximately 90° to 110°. Any compatible hydrocarbon solvent such as toluene or xylene may be used as the reaction medium and the methylating agent may be one of those known to those skilled in the art such as trimethylphenyl ammonium chloride, trimethylphenyl ammonium ethoxide, diazomethane or dimethyl sulfate. After the methylation reaction has been carried out for a sufficient time period, usually two to six hours, the reaction mixture is cooled to a temperature of approximately 50° to 85° C. and water is added to terminate the reaction. Due to the basic nature of the methylating solution, the resulting toluene-water mixture is basic with a pH of approximately 9–10. A small portion of sodium hydroxide or other alkaline material is added to render the mixture more strongly basic with a pH of approximately 11–12. At this pH, unreacted morphine is soluble in water and separation of the water and toluene phases effects a separation of unreacted morphine and codeine.

The toluene phase contains both codeine and dimethylaniline which is left over after the methylating solution of trimethylphenyl ammonium ethoxide has reacted and is neutralized. Dimethylaniline is slightly less basic than codeine and remains in the free base form at a pH of 5.0 to 6.0, while codeine is in the salt form in this pH range. As a salt, codeine is water-soluble and as a free base, the dimethylaniline is soluble in toluene in this pH range. In accordance with the invention, in order to effect a separation of dimethylaniline and codeine, a dilute mineral or organic acid is added to adjust the pH to approximately 4.0 to 6.0 and approximately six to seven times the volume of water for each volume of hydrocarbon solvent is added to effect a separation of dimethylaniline and codeine in the hydrocarbon solvent phase. For this purpose, any dilute mineral or organic acid such as acetic acid, sulfuric acid or hydrochloric acid may be used.

In carrying out the present invention, the morphine starting material may be highly purified or of technical grade and may be in the form of a stable monohydrate containing 5.9% water by weight or even greater levels of water.

In accordance with the invention, the control of codeine methyl ether formation, the removal of unreacted morphine, dimethylaniline and color bodies formed during the methylation reaction advantageously allows for the remaining codeine to be de-colorized via chromatography or other means known to those skilled in the art.

The following examples illustrate the practice of the invention:

EXAMPLE 1

A one-liter flask was charged with 525 ml. of toluene. Either fresh toluene or toluene containing a small portion of codeine from previous use may be employed. 46.5 grams (0.163) gram-moles) of morphine was added to the toluene. The morphine may also contain various amounts of codeine and, in this example, 11.1 grams of codeine (0.037 gram-moles) were part of the morphine charge.

The resulting toluene-morphine slurry was heated and stirred to a temperature of 111° C. with azeotropic removal of the contained water and under reflux conditions whereby more than 50% of the toluene portion was returned from the azeotrope to the slurry.

A methylating slurry was prepared as follows: 28.0 grams (0.163 gram-moles) of a commercial grade of trimethylphenyl ammonium chloride was combined with 60.8 mL or 0.163 gram-moles of a 21% commercial solution of sodium ethoxide in ethanol. 95 mL of ethanol was added to complete the mixture.

The methylating slurry was added to the dehydrated morphine slurry in toluene at a temperature of 90 to 105° C. over the course of one hour. The addition time minimum is 0.5 hours. The condenser setup included enough surface area to return more than 50% of the toluene distilled back to the reaction medium while driving off the lower boiling ethanol. Ethanol is part of the methylating solution, but is also a by-product of the reaction between morphine and ethoxide anion. The addition of the methylating solution may occur over a period of 0.5 to 3 hours. 18 ml. of ethanol was used to rinse the addition apparatus. After addition and rinse, the reaction mixture was heated to 110° C.

The mixture was then cooled to a temperature of 85° C. or less, and 200 ml of water was added as a quenching fluid to terminate the reaction. The resulting two phase system had a pH of 9.13. Two ml. of a 25% solution of sodium hydroxide in water was added to the toluene phase and the resulting mixture had a pH of 11.7. After stirring this mixture for a few minutes to insure good liquid-to-liquid contact, the phases were allowed to settle and then separated. The aqueous phase contained any unreacted morphine, approximately 5.5% in this example, and the toluene phase contained codeine and dimethylaniline.

The toluene phase (375 ml) was mixed with 3 liters of water or an aqueous process stream containing codeine. 70 ml of a 3N solution of sulfuric acid was added with stirring to the mixture of toluene and water and the resulting mixture had a pH of 5.7. This pH may range from approximately 4.0 to 6.0, preferably from approximately 5.0 to 5.7. The phases were allowed to settle and then separated. The aqueous phase containing codeine was separated and measured at 3273 ml. The codeine solution is about 15–20 mg/ml and is suitable for decolorization and isolation.

EXAMPLE 2

A laboratory reaction vessel is charged with 300 ml. of toluene. The toluene used can be fresh or contain a small portion of codeine from previous use. 33.7 grams (0.118 gram-moles) of morphine was added to the toluene. The morphine used can be highly purified or of technical grade. The morphine also contained 6.6 grams (0.022 gram-moles) of codeine. The azeotropic removal of water by heating prior to the methylation reaction removed the water of hydration from the morphine under reflux conditions such that there was a return of more than 50% of the toluene to the reaction slurry.

A methylating slurry was prepared as follows: 20.2 grams (0.118 gram-moles) of a commercial grade of trimethylphenyl ammonium chloride was combined with sodium ethoxide in ethanol. A 21% solution of the commercial grade was used in the amount of 44.0 ml. or 0.118 moles of sodium ethoxide. 68 ml of ethanol was used to complete the mixture.

To the above morphine slurry was added the methylating slurry steadily over a period of two hours and ten minutes. This time may vary from an effective minimum of about 0.5 hours to a period with no upper limit. The addition of the methylating slurry is done under 100% reflux return in this example. After this addition, a 15 ml rinse of ethanol was done to insure complete transfer of the methylating slurry. The reflux/reaction temperature fell to approximately 84.8° C. after the rinse and the reaction mixture was then heated to 110° C. under distillation conditons. The reaction mixture was then cooled to approximately 86° C. and quenched by the addition of 150 ml. of deionized water. About 1 ml. of a 25% sodium hydroxide solution was added to make the mixture alkaline, and the pH of the adjusted mixture was 11.4, the aqueous layer from the reaction mixture was separated after settling for two hours. The unreacted morphine content was recovered by adding ammonium sulfate to the aqueous alkaline phase to a pH of 9.08.

After removal of the aqueous phase, the toluene/ dimethylaniline/codeine phase was mixed with 2 liters of deionized water and adjusted to a pH of 5.7 with diluted sulfuric acid. The layers were separated with the aqueous phase containing the codeine from the methylation reaction. The codeine solution is about 15–20 mg/ml and is suitable for decolorization and isolation.

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

What is claimed is:

1. A process for the preparation of codeine from morphine which comprises the steps of
    a) reacting morphine with a methylating agent in the presence of a hydrocarbon solvent at a temperature of approximately 90° to 110° C. under reflux conditions such that approximately 50% or more of the hydrocarbon solvent is returned to the reaction mixture to substantially avoid the formation of codeine methyl ether; and
    b) recovering codeine from the reaction mixture.

2. A process as set forth in claim 1 wherein said methylating agent is selected from the group consisting of trimethylphenyl ammonium chloride, trimeethylphenyl ammonium ethoxide, diazomethane and dimethyl sulfate.

3. A process as set forth in claim 1 wherein said hydrocarbon solvent is selected from the group consisting of toluene and xylene.

4. A process as set forth in claim 1 wherein said reflux conditions include the provision of two theoretical plates in the overhead condenser in order to insure adequate return of said hydrocarbon solvent to the reaction mixture.

5. A process as set forth in claim 2 wherein said methylating agent is trimethylphenyl ammonium ethoxide.

6. A process as set forth in claim 3 wherein said hydrocarbon solvent is toluene.

7. A process for the preparation of codeine from morphine which comprises the steps of
  a) reacting morphine in a hydrocarbon solvent with a methylating agent in ethanol at a temperature of approximately 90° to 110° C. under reflux conditions such that approximately 50% or more of the hydrocarbon solvent is returned to the reaction mixture to substantially avoid the formation of codeine methyl ether;
  b) cooling the reaction mixture to approximately 50° to 85° C. and adding water to terminate the reaction;
  c) raising the pH of the reaction mixture to approximately 11–12; and
  d) separating the hydrocarbon solvent phase containing codeine and dimethylaniline from the aqueous phase containing unreacted morphine; and
  e) adding a dilute mineral or organic acid to adjust the pH within the range of approximately 4.0 to 6.0 and adding approximately 6 to 7 times the volume of water for each volume of hydrocarbon solvent to effect a separation of dimethylaniline and codeine in the hydrocarbon solvent phase.

8. A process as set forth in claim 7 wherein said methylating agent is selected from the group consisting of trimethylphenyl ammonium chloride, trimethylphenyl ammonium ethoxide, diazomethane and dimethyl sulfate.

9. A process as set forth in claim 7 wherein said hydrocarbon solvent is selected from the group consisting of toluene and xylene.

10. A process as set forth in claim 7 wherein said reflux conditions include the provision of two theoretical plates in the overhead condenser in order to insure adequate return of said hydrocarbon solvent to the reaction mixture.

11. A process as set forth in claim 8 wherein said methylating agent is trimethylphenyl ammonium ethoxide.

12. A process as set forth in claim 9 wherein said hydrocarbon solvent is toluene.

13. A process as set forth in claim 7 wherein said dilute mineral or organic acid is selected from the group consisting of acetic acid, sulfuric acid and hydrochloric acid.

14. In a process for preparing codeine from morphine by reacting morphine with a methylating agent in the presence of a hydrocarbon solvent at a temperature of approximately 90° to 110° C., the improvement which comprises carrying out said reaction under reflux conditions such that approximately 50% or more of the hydrocarbon solvent is returned to the reaction mixture to substantially avoid the formation of codeine methyl ether.

15. A process as set forth in claim 14 wherein said methylating agent is selected from the group consisting of trimethylphenyl ammonium chloride, trimethylphenyl ammonium ethoxide, deazomethane and dimethyl sulfate.

16. A process as set forth in claim 14 wherein said hydrocarbon solvent is selected from the group consisting of toluene and xylene.

17. In a process for preparing codeine from morphine by reacting morphine with a methylating agent in the presence of a hydrocarbon solvent at a temperature of approximately 90° to 110° C., cooling the reaction mixture to approximately 50° to 85° C. and adding water to terminate the reaction, raising the pH of the reaction mixture to approximately 11–12, and separating the resulting hydrocarbon solvent phase from the aqueous phase, the improvement which comprises adding a dilute mineral or organic acid to adjust the pH to within approximately 4.0 to 6.0 and adding approximately 6 to 7 times the volume of water for each volume of hydrocarbon solvent to effect a separation of dimethylaniline and codeine in said hydrocarbon solvent phase.

18. A process as set forth in claim 17 wherein said methylating agent is selected from the group consisting of trimethylphenyl ammonium chloride, trimethylphenyl ammonium ethoxide, diazomethane and dimethyl sulfate.

19. A process as set forth in claim 17 wherein said hydrocarbon solvent is selected from the group consisting of toluene and xylene.

20. A process as set forth in claim 17 wherein said dilute mineral or organic acid is selected from the group consisting of acetic acid, sulfuric acid and hydrochloric acid.

* * * * *